(12) United States Patent
Zander

(10) Patent No.: US 8,932,826 B2
(45) Date of Patent: Jan. 13, 2015

(54) METHOD FOR SIMULTANEOUSLY DETERMINING MULTIPLE COAGULATION PROTEASES

(75) Inventor: Norbert Zander, Marburg (DE)

(73) Assignee: Siemens Healthcare Diagnostics Products GmbH, Marburg (DE)

(*) Notice: Subject to any disclaimer, the term of this patent is extended or adjusted under 35 U.S.C. 154(b) by 3 days.

(21) Appl. No.: 13/327,092

(22) Filed: Dec. 15, 2011

(65) Prior Publication Data

US 2012/0156708 A1    Jun. 21, 2012

(30) Foreign Application Priority Data

Dec. 20, 2010  (EP) .................................... 10195869

(51) Int. Cl.
| | | |
|---|---|---|
| *C12Q 1/56* | (2006.01) | |
| *C12Q 1/37* | (2006.01) | |
| *C12N 9/74* | (2006.01) | |
| *C12N 9/68* | (2006.01) | |
| *C12N 9/50* | (2006.01) | |
| *A61K 38/36* | (2006.01) | |
| *A61K 38/57* | (2006.01) | |

(52) U.S. Cl.
CPC ... *C12Q 1/56* (2013.01); *C12Q 1/37* (2013.01)
USPC .............. 435/13; 435/23; 435/214; 435/217; 435/219; 514/13.7; 514/14.7

(58) Field of Classification Search
CPC .. C07D 413/14; C07D 409/12; C07D 413/12; C12Q 1/37; C12Q 2337/12; C12Q 1/56
See application file for complete search history.

(56) References Cited

U.S. PATENT DOCUMENTS

| | | |
|---|---|---|
| 4,440,678 A | 4/1984 | Svendsen |
| 4,508,644 A | 4/1985 | Heber et al. |
| 4,598,043 A | 7/1986 | Svendsen |
| 5,334,506 A | 8/1994 | Stuber et al. |
| 5,478,810 A | 12/1995 | Stuber et al. |
| 5,510,243 A | 4/1996 | Boyd et al. |

FOREIGN PATENT DOCUMENTS

| | | |
|---|---|---|
| EP | 0258784 | 3/1988 |
| EP | 1833982 | 9/2007 |
| WO | 2004041840 | 5/2004 |
| WO | 2006072602 | 7/2006 |

OTHER PUBLICATIONS van Wijk et al., Clin. Chem., 26(7):885-890, 1980.*
Rosen, Hamostaseologie, 25:259-266, 2005.*
Bates et al., Circulation, 112:e53-e60, 2005.*
EP Search Report for EP App. No. 1015869, dated Apr. 15, 2011.
Kojima, Hirotatsu et al., "Fluorescent Indicators for Nitric Oxide Based on Rhodamine Chromophore," Tetrahedron Letters, vol. 41, No. 1, Elsevier, 4 pages, 2000.
Nguyen, Kiet T. et al., "Slow-Binding Inhibition of Peptide Deformylase by Cyclic Peptidomimetrics as Revealed by a New Spectrophotometric Assay," Bioorganic Chemistry, vol. 32, No. 3, 14 pages, Jun. 1, 2014.

* cited by examiner

*Primary Examiner* — Jennifer McDonald
*Assistant Examiner* — Qing Xu
(74) *Attorney, Agent, or Firm* — King & Spalding L.L.P.

(57) ABSTRACT

The present invention relates to a chromogenic method for simultaneously determining the activity of multiple coagulation proteases or for simultaneously determining the inhibition of multiple coagulation proteases in a single test reaction. For this purpose, use is made of two chromogenic substrates which have different absorption maxima and whose color signals can be separated spectrally.

5 Claims, 1 Drawing Sheet

METHOD FOR SIMULTANEOUSLY DETERMINING MULTIPLE COAGULATION PROTEASES

The present invention is in the field of coagulation diagnostics and relates to a method for simultaneously determining the activity of multiple coagulation proteases or for simultaneously determining the inhibition of multiple coagulation proteases.

Established anticoagulant therapies aim primarily to inhibit the procoagulatory coagulation factors thrombin (factor IIa) and factor Xa. A distinction is made between oral anticoagulation with vitamin K antagonists, such as Coumadin for example, resulting in inhibition of coagulation factor synthesis, and anticoagulation by inhibition of active coagulation factors in the bloodstream. In the case of the anticoagulants which inhibit or inactivate active coagulation factors in the bloodstream, a distinction is made between anticoagulants having a direct effect and those having an indirect effect. Anticoagulants having a direct effect, such as rivaroxaban, dabigatran or melagatran for example, bind to thrombin or factor Xa and are therefore highly specific. Anticoagulants having an indirect effect, such as heparins for example, bind to endogenous coagulation factor inhibitors, such as antithrombin for example, and intensify the anticoagulatory effect thereof many times over.

All anticoagulants which inhibit active coagulation factors in the bloodstream are characterized by a specific inactivation pattern. Certain substance classes, such as unfractionated, high-molecular-weight heparins for example, inhibit both thrombin and factor Xa. Other substances have a highly specific effect, i.e., inhibit either thrombin (e.g., hirudin, dabigatran, melagatran) or factor Xa (e.g., pentasaccharides such as fondaparinux, rivaroxaban).

During the course of treatment of a thromboembolic disease, the anticoagulant is sometimes changed. A classic case is the transition from heparin (inhibition of thrombin and factor Xa in the bloodstream) to Coumadin (inhibition of coagulation factor synthesis in the liver) when treating deep vein thromboses in legs. With such changes in therapy, the relative inactivation of thrombin and factor Xa in the bloodstream can change. For the control of the therapy and the dosing of the medicaments, it is important to know the activity or the inhibition of thrombin and of factor Xa. Therefore, it is necessary to be able to reliably determine the activity or the inhibition of the active coagulation factors thrombin and factor Xa in the blood of a patient.

In coagulation diagnostics, a distinction is made between "global tests" for examining the functionality of the blood coagulation cascade and "individual tests" for determining the activity of individual blood coagulation factors. Different test formats are known both for the global tests and for the individual tests. With regard to the test format, a distinction is essentially made between coagulation tests and chromogenic tests.

In a chromogenic test, the patient sample to be examined, which usually consists of plasma, is mixed with a coagulation activator and with a substrate for a coagulation factor. Since most blood coagulation factors are serine endopeptidases, i.e., hydrolases which can cleave peptide bonds, use is mainly made of peptide substrates which are cleaved highly specifically by the blood coagulation factor to be determined and which have a detectable signal group. Preferably, use is made of cleavable chromogenic or fluorogenic signal groups, which are determined photometrically. Patent documents EP 0034122 A1 and U.S. Pat. No. 4,508,644 describe a multitude of chromogenic peptide substrates and their use in coagulation diagnostic tests, for example for determining the proteolytic coagulation factors factor IIa (thrombin) and Xa. Document EP 0078764 A1 describes a chromogenic method for determining the proteolytic coagulation factor XIIa.

Chromogenic tests in particular can also be used to determine anticoagulants, which inhibit the activity of blood coagulation factors, in patient samples. For this purpose, the patient sample to be examined is usually mixed with an activated coagulation factor and with a substrate for said coagulation factor. The more anticoagulant present in the sample, the greater the inhibition of the activated coagulation factor and the less substrate cleaved.

Established chromogenic tests, which are also commercially available, use in particular the chromophores paranitroaniline (pNA) and 5-amino-2-nitrobenzoic acid (ANBA), which have an absorption maximum at 405 nm. The resulting yellow color is generally determined photometrically. When determining anticoagulants, the color concentration in the test reaction is inversely proportional to the anticoagulant concentration in the sample.

To determine the inhibition of thrombin and factor Xa, it is necessary to carry out two separate tests in which the inhibition of one of the two coagulation factors is determined in each case. It would be desirable to simultaneously determine the activity or inhibition of the two coagulation factors in a single test reaction. This would have the advantages of reducing material consumption and time expenditure and of carrying out both determinations under the same conditions, avoiding variations while carrying out the tests, such as pipetting errors for example, which might lead to an error in determining the relation between the two results.

The object of the present invention is, therefore, to provide a method which allows the simultaneous determination of thrombin and factor Xa in a single test reaction. WO 2006/072602 A1 describes a method for simultaneously determining thrombin and plasmin, an enzyme of the fibrinolytic system, wherein fluorescent substrates are used.

The object underlying the invention is achieved by mixing a sample with a first chromogenic substrate specific for the first proteolytic coagulation factor and with a second chromogenic substrate specific for the second proteolytic coagulation factor, wherein the first chromogenic substrate has a chromophore whose absorption maximum differs by at least 100 nm from the absorption maximum of the chromophore of the second chromogenic substrate. The resulting chromogenic signals can be separated spectrally and can be determined photometrically, independently of one another, at different wavelengths.

The present invention thus provides a method for simultaneously determining the activity of a first proteolytic coagulation factor and of a second proteolytic coagulation factor in a single test reaction, wherein a sample is mixed with a first chromogenic substrate specific for the first proteolytic coagulation factor and with a second chromogenic substrate specific for the second proteolytic coagulation factor, and wherein the absorption change in the test reaction (color signal formation) is determined photometrically, and wherein the first chromogenic substrate has a chromophore whose absorption maximum differs by at least 100 nm from the absorption maximum of the chromophore of the second chromogenic substrate.

The term "proteolytic coagulation factor" is to be understood to mean any plasma serine protease which has a procoagulatory (coagulation-promoting), anticoagulatory (coagulation-inhibiting) or fibrinolytic (clot-degrading) function in a mammalian, preferably human, blood coagulation system.

Procoagulatory proteolytic coagulation factors are, for example, factor IIa (thrombin), factor VIIa, factor IXa, factor Xa, factor XIa, and factor XIIa. An anticoagulatory proteolytic coagulation factor is, for example, protein Ca (activated protein C). A fibrinolytic proteolytic coagulation factor is, for example, plasmin.

The term "simultaneous determination" is to be understood to mean the determination of the two proteolytic coagulation factors in a single test reaction.

In the context of the invention, a "sample" is to be understood to mean the material which is suspected of containing the proteolytic coagulation factors to be detected or the anticoagulant(s) to be determined. The term "sample" comprises in particular human or animal body fluids, especially blood and plasma.

A "chromogenic substrate specific for a proteolytic coagulation factor" is to be understood to mean a substrate which is converted with sufficient specificity by a proteolytic coagulation factor, wherein a chromophore is released as a result of the specific substrate conversion. Cleavable substrates, in particular, which have at least one cleavage site for an activated coagulation factor, are sufficiently known to a person skilled in the art. A cleavable substrate can be a molecule which is broken down into two cleavage products by the action of the activated proteolytic coagulation factor, which molecule is a molecule which has been prepared synthetically, recombinantly or using biotechnological methods or is a natural molecule. A cleavable substrate can entirely or partly consist of a peptide. Preferably, it comprises a peptide portion at least in the region of the cleavage site. Preferably, the peptide portion of a cleavable substrate consists of 3 to about 150 amino acid residues. Patent documents EP 0034122 A1 and U.S. Pat. No. 4,508,644 describe a multitude of chromogenic peptide substrates, their preparation, and their use in coagulation diagnostic tests, for example for determining the coagulation factors factor IIa (thrombin) and Xa. Document EP 78764 A1 describes a chromogenic method for determining the coagulation factor XIIa.

A "chromophore" is to be understood to mean a signal group ("label") which can be cleaved (dissociated) from the substrate by the action of a specific proteolytic coagulation factor and which, after cleavage of the substrate, has absorption properties different from those in the uncleaved state. According to the invention, the first chromogenic substrate has a chromophore whose absorption maximum, after cleavage, differs by at least 100 nm from the absorption maximum of the chromophore of the second chromogenic substrate after cleavage. Table 1 shows a selection of known chromophores, their absorption maxima after cleavage, and preferred combinations of chromophores whose absorption maxima differ by at least 100 nm from one another. Preferred chromophores are those which, after cleavage from the substrate, have an absorption maximum in the visible wavelength range from 380 nm to 780 nm.

The activity of the coagulation factors is determined by photometric determination of absorption change (color signal formation) in the test reaction, which change is proportional to the activity of the coagulation factors. The term "photometric determination of absorption change" is to be understood to mean an absorption measurement in which the reduction in intensity of a light beam transmitted through the test reaction is measured (transmission measurement). In order to measure the color signal formation, a wavelength region is selected which is absorbed by the dissociated chromophore to be determined.

According to the invention, photometric determination of absorption change comprises absorption measurement of the test reaction at least two different wavelengths, which preferably lie in the region of the absorption maxima of the chromophores used. Alternatively, the test reaction can be illuminated with white light, which is broken down spectrally after passage through the test reaction. Measurement of the absorption change of the test reaction over time can be achieved by means of alternating pulses of light of wavelengths corresponding to the absorption maxima of the two chromophores used, the pulses alternating at short intervals.

TABLE 1

| Chromophore | Absorption maximum | Combinable with |
|---|---|---|
| para-Nitroaniline (pNA) | 405 nm | Color Index Basic Blue 49 or 124 |
| 5-Amino-2-nitrobenzoic acid (ANBA) | 405 nm | Color Index Basic Blue 49 or 124 |
| Color Index Basic Blue 49 | 625 nm | pNA, ANBA |
| Color Index Basic Blue 124 | 625 nm | pNA, ANBA |

Particularly preferred chromophores are phenoxazine derivatives, such as, for example, Color Index Basic Blue 49 (C.I. Basic Blue 49, CAS registration number 11075-19-7) or Color Index Basic Blue 124 (C.I. Basic Blue 124, CAS registration number 89106-91-2), which have an absorption maximum of about 600 nm and bring about blue coloration. Patent document EP 0258784 A2 discloses particularly preferred phenoxazine derivatives and correspondingly labeled peptide substrates.

The method according to the invention can be used for simultaneously determining the activity of two proteolytic coagulation factors which are present in the sample of a patient in order to examine the coagulation status of a patient. For this purpose, the sample is usually mixed, before the addition of the two chromogenic substrates, with one or more agents which bring about direct or indirect activation of the proteolytic coagulation factors to be determined. Direct activation is to be understood to mean that an agent is used which directly activates the proteolytic coagulation factor to be determined, independently of the presence of other coagulation factors. Indirect activation is to be understood to mean that an agent is used which activates one or more blood coagulation factors of the blood coagulation cascade, which in turn activate the proteolytic coagulation factor to be examined. The type of agent depends on which coagulation factor is to be determined, whether the activity of the coagulation factor is to be determined on its own, or whether the functionality of the blood coagulation cascade or of a section of the blood coagulation cascade (extrinsic or intrinsic pathway) is to be determined on the basis of a coagulation factor. Substances and specific mixtures of various substances which enable direct or indirect activation of proteolytic coagulation factors are sufficiently known to a person skilled in the art and comprise, for example, phospholipids, such as negatively charged phospholipids for example; lipoproteins, such as thromboplastin for example; proteins, such as tissue factor for example, activated serine proteases, such as, for example, factor IIa (thrombin), factor VIIa, factor IXa, factor Xa, factor XIa, factor XIIa, or activated protein C; snake poisons, such as, for example, PROTAC® enzyme, ecarin, textarin, noscarin, batroxobin, thrombocytin, or Russell's viper venom (RVV); contact activators, such as, for example, silica, kaolin, ellagic acid, or Celite. Further substances which may contain an activating agent are, for example, buffer substances, salts, detergents, ions, in particular calcium ions, and chelating agents.

In one embodiment, an inhibitor of fibrin aggregation can be additionally added to the test reaction. A fibrin aggregation inhibitor is to be understood to mean a substance, in particular a synthetic oligopeptide, which inhibits the association (polymerization) of fibrin monomers formed by the action of thrombin and thus prevents clot formation in the reaction mixture, which might impair photometric determination of color signals (see, for example, EP 0456152 B1).

Furthermore, the method according to the invention can be used for simultaneously determining the activity of two proteolytic coagulation factors which have been added to the sample of a patient in order to examine the anticoagulatory potential of a patient. For this purpose, the patient sample is mixed with defined amounts of at least two procoagulatory proteolytic coagulation factors and with the two chromogenic substrates specific for the coagulation factors added, and the inhibition of the proteolytic activity of the coagulation factors is determined. The greater the anticoagulatory potential of the patient, i.e., the more anticoagulant present in the sample, the greater the inhibition of the activated procoagulatory coagulation factor(s) and the less substrate cleaved. The inhibition of the proteolytic activity of the coagulation factors can be quantified by comparison with a control test reaction in which a normal sample containing no anticoagulant, for example normal human plasma, is used as a sample.

Which activated coagulation factors are added depends on which anticoagulants are to be determined.

For the determination of a heparin, i.e., a high-molecular-weight, unfractionated heparin (HMW heparin) or a low-molecular-weight heparin (LMW heparin) or a heparinoid, it is particularly useful to add factor IIa (thrombin) or factor Xa. For the determination of a direct thrombin inhibitor, for example argatroban, melagatran, ximelagatran, bivalirudin, dabigatran or hirudin, it is particularly useful to add factor IIa (thrombin). For the determination of a direct factor Xa inhibitor, for example rivaroxaban, it is particularly useful to add factor Xa.

The present invention further relates to a test kit for determining the anticoagulatory potential of a patient sample. A test kit according to the invention comprises a first reagent having a defined concentration of a first proteolytic coagulation factor, and a second reagent having a defined concentration of a second proteolytic coagulation factor, and
  a) a third reagent containing a first chromogenic substrate specific for the first proteolytic coagulation factor and a second chromogenic substrate specific for the second proteolytic coagulation factor; or
  b) a third reagent containing a first chromogenic substrate specific for the first proteolytic coagulation factor and a fourth reagent containing a second chromogenic substrate specific for the second proteolytic coagulation factor,
wherein the first chromogenic substrate has a chromophore whose absorption maximum differs by at least 100 nm from the absorption maximum of the chromophore of the second chromogenic substrate.

In a preferred test kit, the first chromogenic substrate specific for the first proteolytic coagulation factor has a chromophore from the group comprising para-nitroaniline and 5-amino-2-nitrobenzoic acid, and the second chromogenic substrate specific for the second proteolytic coagulation factor has a chromophore from the group comprising phenoxazine derivatives, or vice versa.

A particularly preferred test kit comprises a first reagent having a defined thrombin concentration and a second reagent having a defined factor Xa concentration and at least one further reagent containing a thrombin-specific and/or a factor Xa-specific chromogenic substrate, wherein the thrombin-specific chromogenic substrate has a chromophore whose absorption maximum differs by at least 100 nm from the absorption maximum of the chromophore of the factor Xa-specific chromogenic substrate. The two substrates may be present in a single reagent or in separate reagents. Preferably, the thrombin-specific chromogenic substrate has a chromophore from the group comprising para-nitroaniline and 5-amino-2-nitrobenzoic acid, and the factor Xa-specific chromogenic substrate has a chromophore from the group comprising phenoxazine derivatives, or vice versa.

The reagents of the test kit according to the invention may be provided in liquid or lyophilized form. In the event that some or all reagents of the test kit are present as lyophilisates, the test kit may additionally contain the solvents required for dissolving the lyophilisates, such as, for example, distilled water or suitable buffers.

Figure 1:
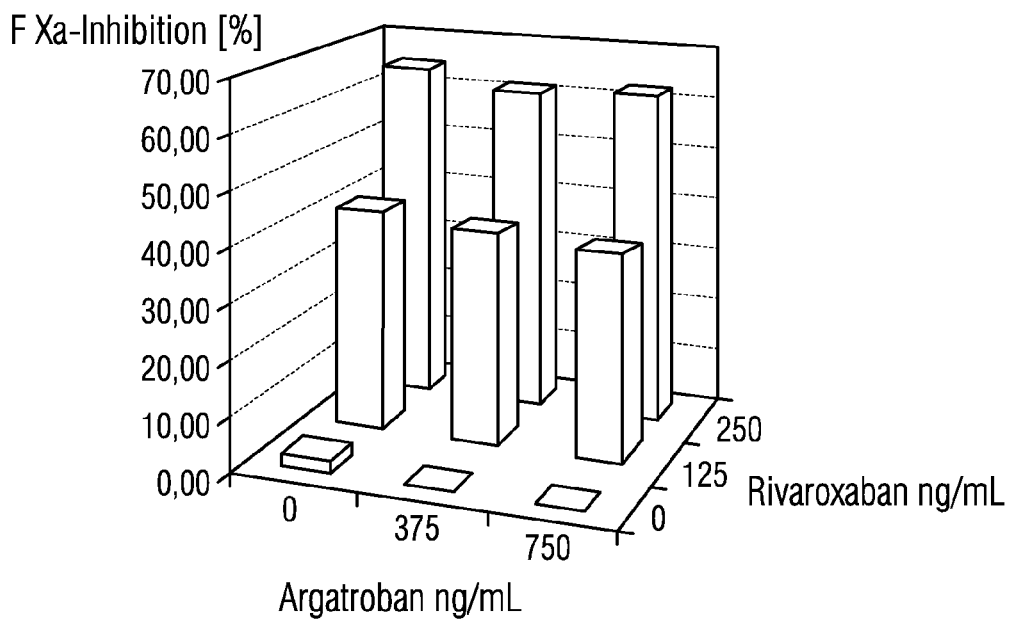
FIG. 1
Figure 2:
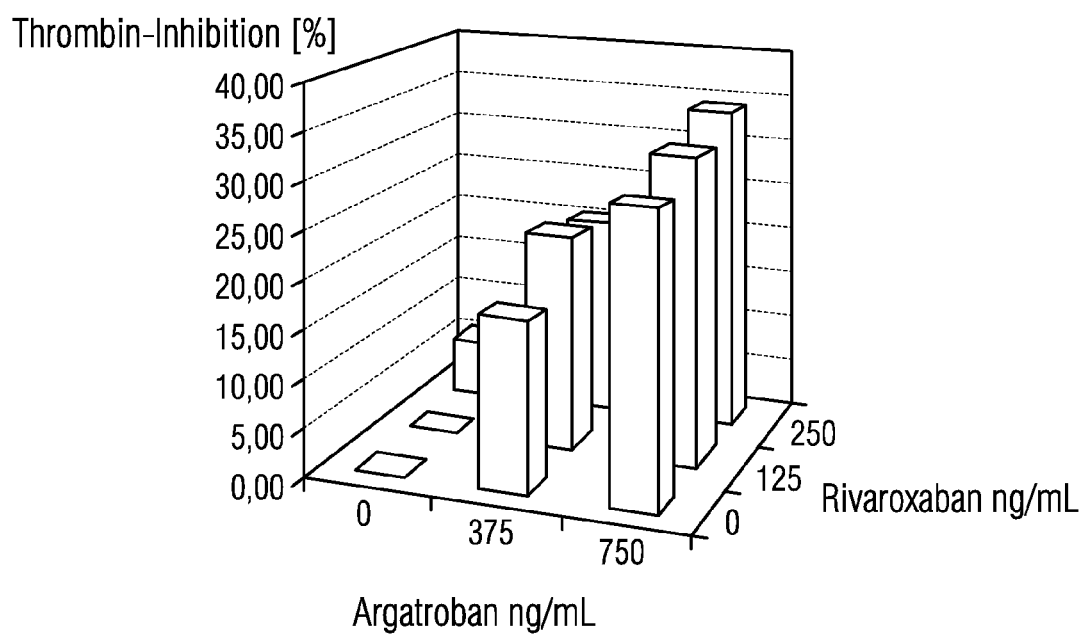

Bar chart showing the inhibition of factor Xa activity [%] in normal plasma samples enriched with rivaroxaban and/or argatroban at various concentrations (see example 2). Cleavage of the factor Xa-specific peptide substrate having an ANBA chromophore was measured at a wavelength of 405 nm. Irrespective of the argatroban concentration (thrombin inhibitor), increased factor Xa inhibition is measured in samples having an increased rivaroxaban concentration (factor Xa inhibitor).

FIG. 2

Bar chart showing the inhibition of thrombin activity [%] in normal plasma samples enriched with rivaroxaban and/or argatroban at various concentrations (see example 2). Cleavage of the thrombin-specific peptide substrate having a Basic Blue 49 chromophore was measured at a wavelength of 575 nm. Irrespective of the rivaroxaban concentration (factor Xa inhibitor), increased thrombin inhibition is measured in samples having an increased argatroban concentration (thrombin inhibitor).

The following exemplary embodiments serve to illustrate the method according to the invention and are not to be understood as limiting.

EXAMPLES

Example 1

Simultaneous Determination of Thrombin Activity and of Factor Xa Activity in Blood Plasma in a Single Reaction The following components were mixed to form one reaction:
10 µl sample
10 µl pool of normal human plasma
40 µl substrate reagent (4 mM Z-D-Leu-Gly-Arg-ANBA-methylamide, 0.8 mM Tos-Gly-Pro-Arg-Basic Blue 49 in mannitol buffer, pH 4.0)
100 µl factor Xa reagent (0.75 U/ml human factor Xa in 4.5 g/l TRIS, 9 g/l NaCl, 0.56 g/l EDTA, pH 8.0)
100 µl thrombin reagent (5 U/ml bovine thrombin in 1.2 g/l TRIS, pH 8.2)

The sample used was normal human plasma. Factor Xa cleaves ANBA from the factor Xa-specific peptide substrate Z-D-Leu-Gly-Arg-ANBA-methylamide, increasing over time the optical density in the reaction at a wavelength of 405 nm. At the same time, thrombin cleaves Basic Blue 49 from the thrombin-specific peptide substrate Tos-Gly-Pro-Arg-Basic Blue 49, increasing over time the optical density in the reaction at a wavelength of 575 nm.

The measurements of the optical densities of the reaction at 405 nm and 575 nm and the evaluation of the reaction kinetics were carried out simultaneously in a fully automated Sysmex® CS-2000i coagulation analyzer. To measure the optical densities, the reaction was irradiated alternately with light of the aforementioned wavelengths, and the absorbance of the light, caused by the coloration of the reaction, was determined as a function of wavelength and time.

The increases in the reaction kinetics correlate with the respective enzyme activity. For a normal plasma sample, the factor Xa-specific absorbance change at 405 nm was 0.236 per minute, whereas the thrombin-specific absorbance change at 575 nm was 0.111 per minute.

Example 2

Simultaneous Determination of Thrombin and Factor Xa Inhibitors in a Single Reaction Normal plasma was enriched with various concentrations of rivaroxaban, a specific factor Xa inhibitor, and/or of argatroban, a specific thrombin inhibitor, and used as a sample in a method as per example 1.

The increases in the reaction kinetics for normal plasma without inhibitors were defined as 100% of the respective enzyme activity. The results of the plasma samples having various inhibitor concentrations were evaluated on the basis of this reference. The results (inhibition in %) are summarized in table 2.

TABLE 2

| Rivaroxaban (ng/ml) | Argatroban (ng/ml) | F Xa inhibition [%] | Thrombin inhibition [%] |
|---|---|---|---|
| 0 | 0 | 2 | 0 |
| 0 | 375 | 0 | 18 |
| 0 | 750 | 0 | 31 |
| 125 | 0 | 42 | 0 |

TABLE 2-continued

| Rivaroxaban (ng/ml) | Argatroban (ng/ml) | F Xa inhibition [%] | Thrombin inhibition [%] |
|---|---|---|---|
| 125 | 375 | 40 | 23 |
| 125 | 750 | 39 | 33 |
| 250 | 0 | 65 | 5 |
| 250 | 375 | 62 | 22 |
| 250 | 750 | 63 | 35 |

The results show that the use of two chromogenic substrates having different enzyme specificities and having chromophores which have different absorption maxima allow the simultaneous, independent determination of inhibitors specific for different coagulation factors in a single reaction.

The invention claimed is:

1. A method for simultaneously determining the activity of thrombin and factor Xa in a single test reaction, the method comprising:
   mixing a sample which contains human plasma and which is suspected of containing thrombin and factor Xa with a first chromogenic substrate specific for thrombin and a second chromogenic substrate specific for factor Xa, wherein a chromophore of the first chromogenic substrate and a chromophore of the second chromogenic substrate have respective absorption maximums that differ from each other by at least 100 nm, and
   photometrically determining absorption changes in the test reaction,
   determining the activity of the thrombin and factor Xa in the sample based on the photometrically determined absorption changes.

2. The method as claimed in claim 1, wherein the first or second chromogenic substrate has para-nitroaniline or 5-amino-2-nitrobenzoic acid as a chromophore.

3. The method as claimed in claim 1, wherein the first or second chromogenic substrate has a phenoxazine derivative as a chromophore.

4. The method as claimed in claim 1, wherein thrombin and factor Xa are present in the sample and are activated by the addition of one or more agents for the activation of the coagulation factors.

5. The method as claimed in claim 1, wherein defined amounts of thrombin and factor Xa are mixed with the sample, and wherein an anticoagulant concentration in the sample is determined on the basis of the inhibition of the absorption change.

* * * * *